United States Patent [19]
Patrick

[11] Patent Number: 4,817,438
[45] Date of Patent: Apr. 4, 1989

[54] WATER APPLICATOR FOR PAPER TENSILE STRENGTH TESTER

[76] Inventor: Rodney T. Patrick, 511 Goebel St., Berlin, N.H. 03570

[21] Appl. No.: 187,202

[22] Filed: Apr. 28, 1988

[51] Int. Cl.⁴ .............................................. G01N 3/08
[52] U.S. Cl. ...................................................... 73/835
[58] Field of Search ................ 73/831, 832, 833, 834, 73/835, 826, 837, 838, 840

[56] References Cited

U.S. PATENT DOCUMENTS 2,893,241  7/1959  Fisher et al. ........................ 73/834 X
3,741,005  6/1973  Dauth et al. ........................... 73/831

*Primary Examiner*—Jerry W. Myracle
*Attorney, Agent, or Firm*—Sughrue, Mion, Zinn, Macpeak & Seas

[57] ABSTRACT

A water applicator for securement to a paper tensile strength testing machine may be secured to the testing machine adjacent a dry sheet of paper held under tension by the machine in a vertical plane. The water applicator includes pneumatic actuators for moving a pair of sponges on opposite sides of the sheet of paper into and out of engagement with the sheet of paper. When the sponges are out of engagement with the sheet of paper, a spray nozzle is provided for spraying a predetermined amount of water onto at least one of the sponges so that upon movement of the sponges into pressure engagement with the sheet of paper, a predetermined amount of water will by applied to the paper for subsequent wet paper tensile strength testing.

4 Claims, 3 Drawing Sheets

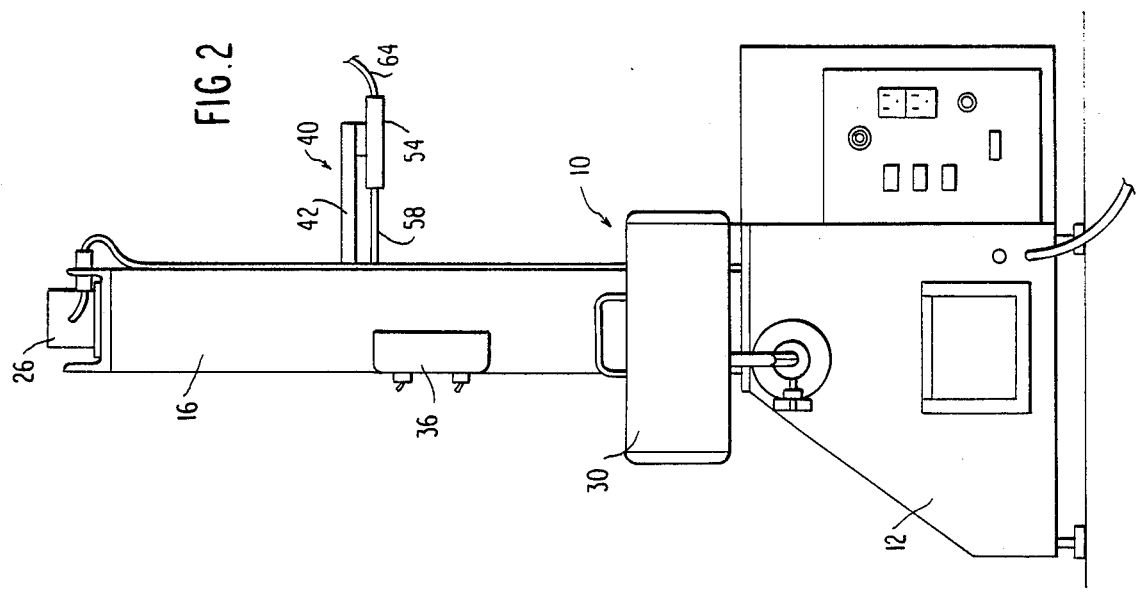
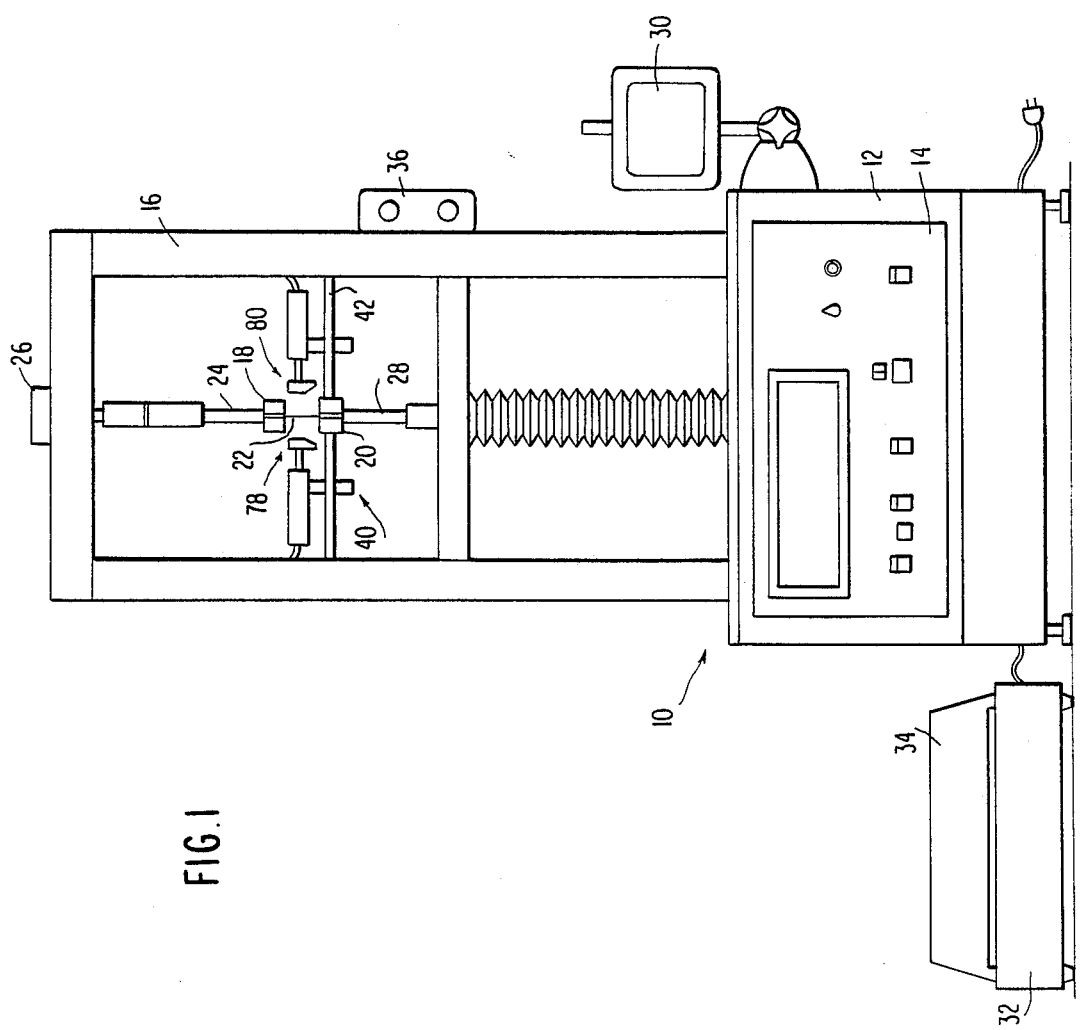

WATER APPLICATOR FOR PAPER TENSILE STRENGTH TESTER

BACKGROUND OF THE INVENTION

The present invention is directed to a water applicator for a paper tensile strength tester and more specifically to a water applicator for providing a controlled uniform amount of water to successive paper samples to be tested when gripped under tension in a testing machine.

Apparatus for testing the tensile strength of sheet material are old and well known in the art and are generally comprised of two, spaced-apart, gripping devices for gripping the sheet of material to be tested and pneumatic or hydraulic means for moving the two gripping devices apart until the sheet of material ruptures. The applied force at the moment of rupture can then be recorded. The Cowan U.S. Pat. No. 3,707,119 is an example of such an apparatus. The sheet of material, however, is tested in the dry condition, and no provision is made for applying water to the sheet of material to test the wet strength of the material.

The use of wet web tensile strength testing devices are also known in the art but generally are provided for testing a wet web or sheet as formed on a wire cloth. The handling of such a wet web or sheet to mount the same in a tensile strength testing machine raises a number of problems since such a wet sheet is extremely weak and easily damaged in handling. In the U.S. patent to Dauth U.S. Pat. No. 3,741,005, the wet web is formed on a Fourdrinier wire or screen. A pair of rollers are superimposed above a table supporting the Fourdrinier wire and means are provided for clamping one end of the wet web between the lower of the two rollers and the wire by the weight of the roller. By means of a suction box affixed to a movable arm, the other end of the web is lifted from the wire above the upper of the two rollers and clamped thereon by means of a spring clamping means. The rollers are then moved apart and the stress applied to the wet specimen is recorded to measure the tensile strength and elongation upon breakage of the specimen. In the Fisher et al. U.S. Pat. No. 2,893,241 the wet web or specimen is formed on a divided forming screen. One half of the screen holding the wet web is held in a fixed position and the other half of the screen is moved away from the fixed path by suitable mechanical means to apply a measured force to the wet web to measure the wet strength of the web. In both of these patents, there is no system for guaranteeing a uniform degree of wetness for the various samples to be tested, and therefore, the measured tensile strength of each specimen could vary widely depending upon the degree of wetness.

SUMMARY OF THE INVENTION

The present invention provides a water applicator for a tensile strength tester whereby a uniform predetermined amount of water will be applied to each sheet of paper to be tested subsequent to the mounting of each dry sheet of paper in a tensile strength testing device. Since each sheet of paper to be tested is mounted in the tensile strength testing machine in the dry state, there is no danger of damaging the sheet of paper to be tested. Furthermore, since each sheet of paper to be tested is wetted with the same predetermined amount of water, each sheet being tested will have the same degree of wetness so that the testing results will not be adversely influenced by varying degrees of wetness.

The present invention provides a water applicator for a paper tensile strength testing machine comprising support means adapted to be secured to a tensile strength testing machine adjacent a pair of spaced-apart gripping devices in the tensile strength testing machine for holding a sheet of paper in a vertically disposed plane, first and second actuator means having movable members mounted on said support means on opposite sides of said vertical plane, a pair of sponge means detachably mounted on said movable members of said first and second actuator means, respectively, for movement toward and away from each other on opposite sides of said vertical plane for movement into and out of engagement with opposite sides of said sheet, and spray means mounted on said support means for spraying a predetermined amount of water on at least one of said sponge means when said sponge means are moved out of engagement with said sheet. Each of the first and second actuator means may be comprised of a first pneumatic actuator having a first movable member movable in a first direction parallel to the vertical plane of the sheet between a first position adjacent to but spaced from the sheet and a retracted position adjacent the spray means and a second pneumatic actuator having a second movable member mounted on said first movable member with the sponge means mounted on the second movable member for movement in a second direction perpendicular to said first direction for moving said sponge means into and out of engagement with the sheet. The sponge means is provided with a specific volume and shape to hold the predetermined amount of water sprayed thereon without dripping and limit means are provided on the sponge means for limiting the movement of the sponge means towards each other on opposite sides of the sheet of paper.

The foregoing and other objects, features and advantages of the invention will be apparent from the following more particular description of a preferred embodiment of the invention as illustrated in the accompanying drawings.

BRIEF DESCRIPTION OF THE DRAWINGS

FIG. 1 is a front elevation view of a tensile strength testing machine with the water applicator for applying water to the sheet of paper to be tested mounted thereon adjacent the means for gripping the sheet of paper.

FIG. 2 is a side elevation view of the apparatus shown in FIG. 1.

DETAILED DESCRIPTION OF THE INVENTION

Figure 3:
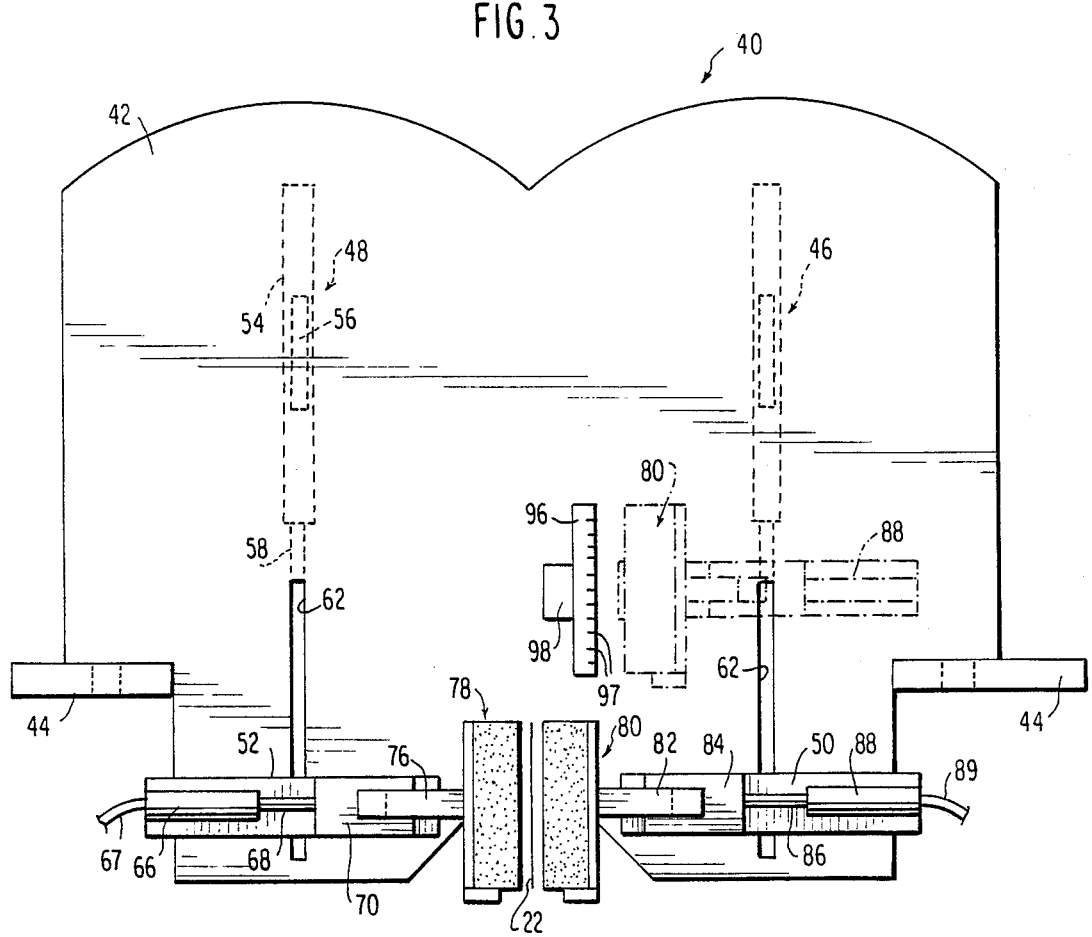
FIG. 3 is a top plan view of the water applicator apparatus according to the present invention.

The tensile strength testing machine as shown in FIGS. 1 and 2 is a conventional well-known testing machine to which the water applicator assembly, according to the present invention, has been attached. The details of the testing machine are old and well-known and it is not deemed necessary to provide a detailed description of the testing machine, since it does not form part of the present invention which is a water applicator apparatus for applying water to the sheet of paper held in the tensile strength testing machine.

The testing machine 10 includes a base member 12 adapted to contain the power supply control circuitry for the machine which is operatively connected to the control panel 14. A vertically extending open rectangular frame 16 is mounted on the upper surface of the base member for supporting a pair of paper gripping jaw assemblies 18 and 20 which hold a sheet of paper 22 to be tested in a vertical plane. The uppermost gripper 18 is mounted in a stationary manner relative to the frame 16 by means of a rod 24 which is effectively connected to a load cell 26 secured to the frame 16. The lower gripper 20 is mounted on the upper end of a rod 28 which is movable vertically in opposite directions by means of a suitable mechanism located within the base 12. Thus, by moving the lower gripper 20 downwardly, the tensile force applied to the paper 22 will be imparted to the rod 24 and the tensile force will be registered by the load cell 26. The value of the load force can be displayed on the CRT display 30. As an optional feature, the load force can be recorded on a recorder 32 and/or printed out by a printer 34. The grippers 18 and 20 can be selectively opened and closed for releasing and gripping a sheet of paper by means of suitable air grip controls 36 mounted on the frame 16 adjacent the grippers.

In order to test the wet strength of the sheet of paper 22, it is necessary to wet the sheet 22 prior to the application of the tensile force. Since it is too difficult to handle a wet sheet of paper without damaging the paper, it is preferable not to wet the sheet of paper until after the sheet of paper has been mounted in the grippers 18 and 20 and held vertically with a minimum tensile force.

In order to achieve some degree of uniformity in the testing operation, it is essential that the same amount of water be applied to each sheet of paper being tested, since the tensile strength of the sheet of paper could vary considerably with different amounts of water absorbed by the sheet of paper.

Figure 4:
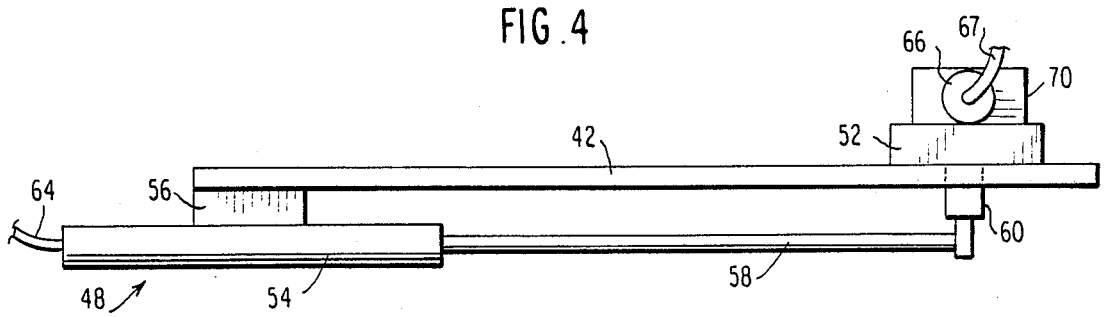
FIG. 4 is a side elevation view of the water applicator apparatus as shown in FIG. 4.
Figure 5:
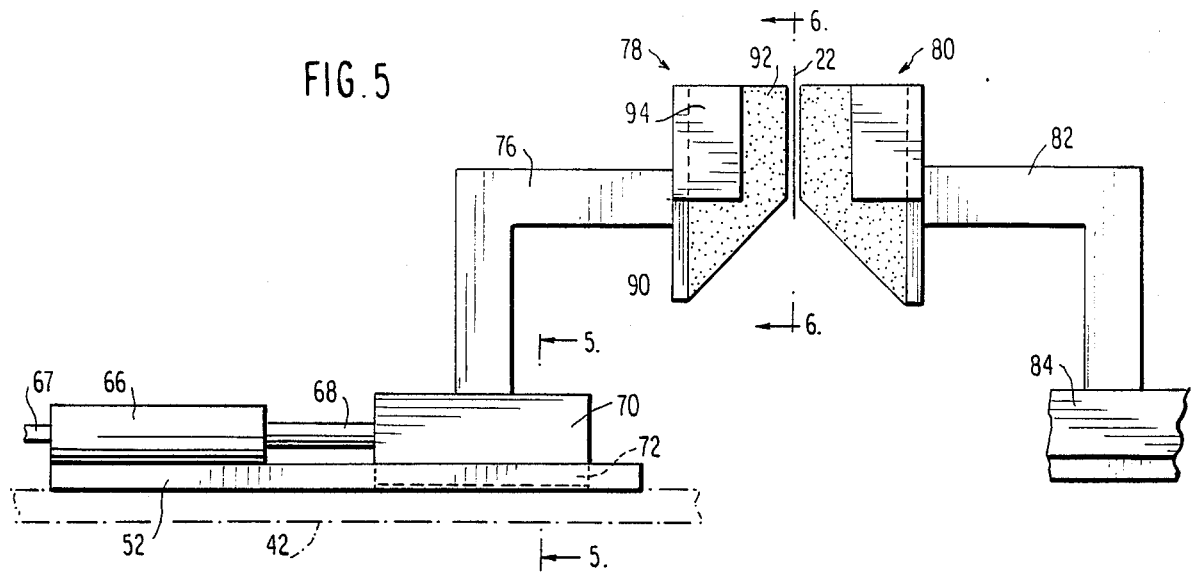
FIG. 5 is a front elevation view of the water applicator apparatus as shown in FIG. 3.

In order to achieve the application of a uniform amount of water to the sheet of paper to be tested, the water applicator apparatus 40 as shown in FIGS. 3-5 can be mounted on the frame 16 of the tensile testing machine. The water applicator apparatus is comprised of a base plate 42, which is adapted to be mounted in a horizontal position on the vertical frame 16 of the tensile strength testing machine 10 by means of bolts (not shown) for securing the brackets 44 to the frame 16.

A first pair of pneumatic actuators 46 and 48 are mounted on the base plate 42 for moving support members 50 and 52 along straight line paths parallel to each other and the vertical plane in which the paper sample 22 is disposed. The pneumatic actuators 46 and 48 are identical to each other and the pneumatic actuator 48, which is shown in FIG. 4, is comprised of a cylinder 54 suspended from the underside of the support plate 42 by means of a bracket 56. One end of a piston assembly 58 is mounted for reciprocation within the cylinder 54 and the other end of the piston assembly 58 is connected to the movable support 50 by means of a connector 60 extending upwardly through a slot 62 in the support plate 42. A conduit 64 adapted to be connected to a pressurized source of air communicates with the interior of the cylinder 54 through one end thereof whereby upon the application of pressurized air to one end of the piston assembly 58, the piston assembly 58 will be moved to the right, as viewed in FIG. 4. Upon discharge of the pressurized air, suitable spring means (not shown) located within the cylinder 54 move the piston assembly 58 in the opposite direction.

Figure 5A:
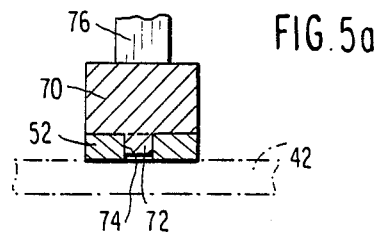
FIG. 5a is a detailed sectional view taken on the line 5—5 in FIG. 5.
Figure 6:
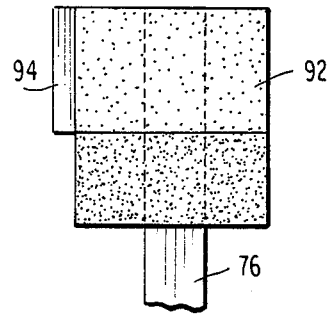
FIG. 6 is a detailed view of the sponge assembly taken along the line 6—6 in FIG. 5.

A second pneumatic cylinder 66 is mounted on one end of the movable support 50 with the axis thereof disposed perpendicular to the axis of the cylinder 54. One end of a piston assembly 68 is slidably mounted in the cylinder 66 and a second movable support 70 is secured to the opposite end of the piston assembly 68. The slidable support member 70 is provided with a downwardly extending projection 72 for sliding movement in a guide slot 74 formed in the first support member 50, as best seen in FIG. 5a. An L-shaped bracket 76 is secured to the upper surface of the second support member 70 and a sponge assembly 78 is detachably secured to the end of the horizontal portion of the bracket 76.

An identical sponge assembly 80 is mounted by means of an L-shaped bracket 82 on a movable member 84 which is slidably mounted on the support member 50 in the same manner in which the support member 70 is slidably mounted on the support member 52. One end of a piston assembly 86 is slidably mounted in a pneumatic cylinder 88 and the opposite end of the piston assembly is secured to the slidable member 84. Each of these cylinders 66 and 88 are connected by conduits 67 and 89, respectively, through a suitable supply of pressurized air for moving the respective piston assemblies toward the paper sample 22 which is located between the two sponge assemblies 78 and 80. Suitable spring means (not shown) are located in the cylinders 66 and 88 for returning the respective piston assemblies in the opposite direction to move the sponge assemblies away from the paper sample 22.

Figure 7:
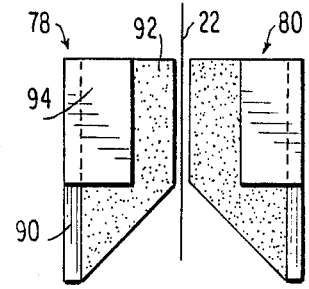
FIG. 7 is a detailed front elevation view of the sponge assemblies as shown in FIG. 5.
Figure 8:
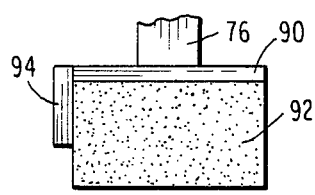
FIG. 8 is a top plan view of a sponge assembly as shown in FIG. 6.

The two sponge assemblies 78 and 80 are identical in construction and only the sponge assembly 78 will be described in detail. The sponge assembly 78 is provided with a vertically disposed support plate 90 which may be detachably secured to the support bracket 76 by means of screws or a dovetailed sliding connection, neither of which have been illustrated. As an alternative arrangement, the support plate 90 could be secured to the support bracket 76, which could be detachably connected to the block 70 by inserting the vertical leg of the bracket 76 into a corresponding support hole in the support block 70. A substantially rectilinear sponge 92 is secured to the support plate 90 by any suitable means such as adhesive or the like. A limit plate 94 is secured to one side of the support plate 90 and has a width substantially half the width of the sponge 92, as best seen in FIGS. 5 and 7. Thus, when the opposing sponges are moved into pressure engagement with the paper sample 22, the amount of pressure supplied to the sponges to squeeze the water out of the sponges, is limited by the abutment of the two limit plates when they simultaneously engage the paper sample 22. The lower portion of the front face of the sponge 92 facing the paper sample 22 is bevelled downwardly from the lower edge of the limit plate 94 to the lower edge of the support plate 90 for reasons set forth hereinafter.

In order to supply water to a sponge assembly, a spray nozzle 96 having a plurality of apertures 97 is mounted on the support plate 42 by means of a hollow support member 98 having suitable water supply conduits extending therethrough, which may be connected to a suitable supply of water under pressure. Suitable metering means (not shown) may be provided which are old and well-known in the art, whereby a predetermined amount of water will be sprayed from the nozzle 96 onto the sponge assembly 80 when the sponge assembly 80 is moved to its completely retracted position by means of the springs located in the cylinders 88 and 66. In this position, the sponge assembly 80 will be disposed directly opposite in close proximity to the nozzle 96, whereby the water will be sprayed onto the vertically disposed surface of the sponge. Although it is possible to provide a second nozzle for applying the predetermined amount of water to the other sponge assembly 78, it has been found to be sufficient to only supply the water to one sponge assembly.

In operation, a dry paper sample 22 is mounted between the grippers 18 and 20 and held taut in a vertical plane with minimal tension applied thereto by the piston assembly 28. In the absence of pressurized air being supplied to the various actuator assemblies, the spring means in the cylinders 66 and 88 will retract the sponge assemblies 78 and 8 away from the paper sample 22 and the spring assemblies in the actuators 46 and 48 will retract the sponge assemblies 78 and 80 to their second position with the sponge assembly 80 disposed opposite the nozzle 96. The water supply controls are then actuated to supply a predetermined amount of water to the sponge 92 of the sponge assembly 80. Before the water held by the sponge can drain by gravity to the bottom portion of the sponge, pressurized air is supplied simultaneously to both assemblies 46 and 48 to move the two sponge assemblies into alignment with the vertically disposed paper sample 22. Pressurized air will then be immediately supplied to the cylinders 66 and 88 to move the sponge assemblies 78 and 80 toward each other into pressure engagement with the paper sample 22. The sponges will be compressed until the limit plates on the two sponge assemblies abut each other. Since the water within the sponge 92 of the sponge assembly 80 tends to drain downwardly due to gravity, the lower portion of the sponge is bevelled away from the paper sample so that less pressure will be applied to the lower portions of the sponge, whereby a uniform amount of water is applied to the paper sample over the entire vertical length of the sponge. The presence of the backing sponge in the sponge assembly 78 helps to evenly distribute the water through the paper sample. The supply of air to the pneumatic cylinders is then terminated to permit the springs to retract the sponge assemblies away from the paper sample. As soon as the sponge assemblies are moved clear of the paper sample 22, the gripper 20 can be moved downwardly to apply a tensile force to the wet paper sample until it ruptures. The amount of tensile force required to rupture the paper will then be transmitted to the CRT display 30 and to the recorder and/or printer assembly 32, 34. The gripper assemblies 18 and 20 can then be opened to permit removal of the ruptured wet paper sample and a new dry paper sample can be clamped by the grippers 18 and 20 for a subsequent testing operation.

While the invention has been particularly shown and described with reference to preferred embodiments thereof, it will be understood by those in the art that the foregoing and other changes in form and details may be made therein without departing from the spirit and scope of the invention.

What is claimed is:

1. A water applicator for a paper tensile strength testing machine of the type having gripping means for holding sheet of paper under tension in a vertical plane comprising support means adapted to be secured to the tensile strength testing machine adjacent the gripping means, first and second actuator means having movable members mounted on said support means on opposite sides of said vertical plane, a pair of sponge means detachably mounted on said movable members of said first and second actuator means, respectively, for movement toward and away from each other on opposite sides of said vertical plane for movement into and out of engagement with opposite sides of said sheet, and spray means mounted on said support means for spraying a predetermined amount of water on at least one of said sponge means when said sponge means are moved out of engagement with said sheet.

2. A water applicator as set forth in claim 1 wherein each of said first and second actuator means is comprised of a first pneumatic actuator having a first movable member movable in a first direction parallel to said vertical plane between a first position adjacent to but spaced from the sheet of paper in a retracted position adjacent the spray means and a second pneumatic actuator having a second movable member mounted on said first movable member with the sponge means mounted on said second movable member for movement in a second direction perpendicular to said first direction for moving said sponge means into and out of engagement with said sheet.

3. The water applicator as set forth in claim 2 wherein each sponge means is comprised of a vertically disposed backing plate adapted to be mounted on said movable member, a substantially rectilinear sponge secured to said backing plate between said backing plate and said vertical plane, a pressure limiting plate secured to said backing plate and extending toward said vertical plane and having a width substantially half the width of the sponge whereby upon movement of said sponge means towards each other said limit plates will engage each other to limit the squeezing of each sponge.

4. A water applicator as set forth in claim 3 wherein the upper portion of the sponge facing said vertical plane is disposed parallel to said vertical plane and the lower portion of said sponge facing said vertical plane is bevelled away from said vertical plane to the bottom of said backing plate.

* * * * *